United States Patent [19]

Eisert

[11] 4,343,551
[45] Aug. 10, 1982

[54] APPARATUS FOR COUNTING AND CLASSIFYING PARTICLES

[75] Inventor: Wolfgang G. Eisert, Hanover, Fed. Rep. of Germany

[73] Assignee: Gesellschaft für Strahlen- und Umweltforschung mbH München, Munich, Fed. Rep. of Germany

[21] Appl. No.: 155,131

[22] Filed: May 30, 1980

[30] Foreign Application Priority Data

Jun. 2, 1979 [DE] Fed. Rep. of Germany ....... 2922643

[51] Int. Cl.³ ...................... G01N 15/02; G01N 21/01
[52] U.S. Cl. ............................. 356/335; 250/222 PC; 356/440
[58] Field of Search .................................. 324/71 CP; 356/335–343, 441, 442, 440; 250/222 PC

[56] References Cited

U.S. PATENT DOCUMENTS

| | | | |
|---|---|---|---|
| 2,535,181 | 12/1950 | Way | 356/246 |
| 2,909,960 | 10/1959 | Orr, Jr. et al. | 356/340 |
| 3,702,403 | 11/1972 | Kishi | 356/246 |
| 4,110,043 | 8/1978 | Eisert | 250/222 PC X |

Primary Examiner—John K. Corbin
Assistant Examiner—Bruce Y. Arnold
Attorney, Agent, or Firm—Spencer & Kaye

[57] ABSTRACT

An apparatus for hydrodynamically focusing particles to permit counting and classification of the particles, which apparatus includes a flow nozzle terminating in a capillary nozzle that forms a thin stream containing the particles and having a circular cross section with the particles oriented along one axis of the thin stream, and a jacket pipe enclosing the capillary nozzle for providing an entraining stream for the thin stream of particles leaving the capillary nozzle, is further provided with a further flow nozzle located downstream of the capillary nozzle and presenting a circular cross section for receiving the stream leaving the capillary nozzle, and changing its cross section from circular to rectangular such that the stream exits from the further nozzle with a rectangular cross section, a device directing a laser beam normally to one flat side of the rectangular cross section at a location downstream of the further nozzle, and a radiation detector disposed for detecting radiation resulting from impingement of laser radiation on particles in the stream of rectangular cross section.

4 Claims, 2 Drawing Figures

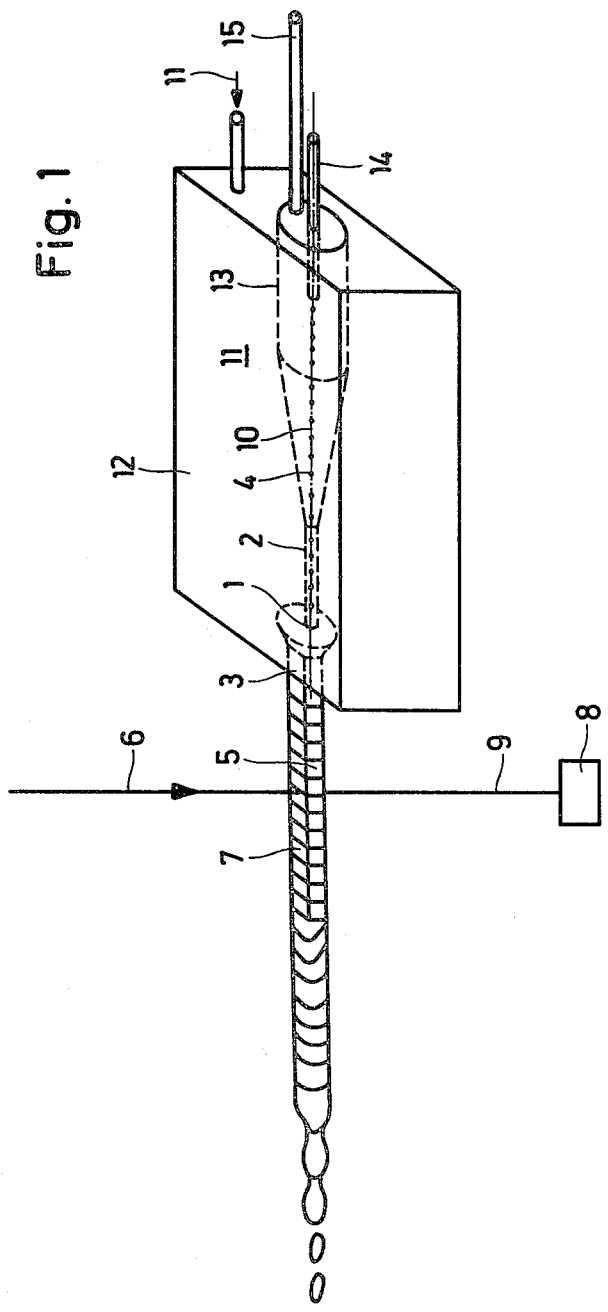
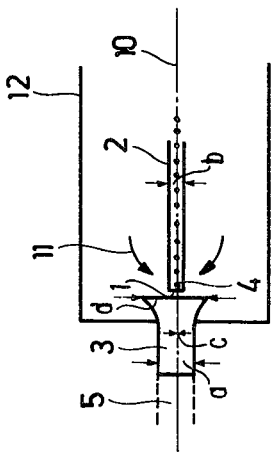

APPARATUS FOR COUNTING AND CLASSIFYING PARTICLES

BACKGROUND OF THE INVENTION

The present invention relates to an apparatus for counting and classifying particles of the type composed of a flow nozzle which hydrodynamically focuses the particles and which opens into a capillary nozzle that generates a thin stream having a circular cross section and containing particles which are aligned along an axis of the thin stream, and a jacket pipe which encloses the capillary nozzle and in which an entraining stream is formed for the thin particle stream.

For various purposes, it is necessary to count and record the size distribution of cells and particles with simultaneous classification according to certain cell characteristics. However, numerous problems have been encountered in procedures thus far devised for performing these operations.

One known process based on the Coulter principle provides for electronic measurement of the cell volume on the basis of changes in resistance of an electrolyte liquid during passage of the cells through an opening in a partition.

It has also been proposed to employ optical flow-through methods which entail fluorescence measurements with colored particles and differentiation according to the intensity of the fluorescence, or scattered light measurements in which a coherent light source is scattered at particles, or measurements of the absorption of the entire cell on object carriers. In all these optical processes the measuring volume is greater, however, than the cell or particle to be measured, respectively.

In measurement procedures according to the Coulter principle, the measured value depends on the geometry of the measuring opening in the partition and on the location of the path of travel of the particles through the measuring opening. No information other than cell volume can be obtained about the particles. Moreover, there exists a danger of the measuring opening becoming clogged and the maxium cell diameter is limited to 50% of the measuring opening. The result is a low counting rate which is still dependent on particle size.

Fluorescence measurements have the drawback that the measured value is dependent of the coloration processes, i.e., different measuring series cannot be directly compared with one another and fluorescence colorations of special cell characteristics can often not be produced at all. In the case of scattered light measurements it is necessary, in order to record a size distribution, to simultaneously effect measurements at various spatial angles. This has the result that only size distributions up to a maximum of about $10\mu$ can be derived from scatter data. In the practice of both of these measuring methods, the particles are present in suspension and the optical quality of the suspension stream is also not optimally adapted to the index of refraction of the cells.

Absorption measurements have in the past been successful only when the measuring field is larger than the cell cross section. The cells are here applied to object carriers, and this results in low counting and analysis speeds since the object carrier must, inter alia, be moved mechanically.

To remedy these deficiencies, a more recently developed apparatus disclosed in German Offenlegungsschrift No. 2,543,310 and counterpart U.S. Pat. No. 4,110,043, performs the optical analysis of cells and particles in a fluid stream for the purpose of separating or enriching, respectively, particles and cells. The cells and particles are formed into a single file stream with the aid of hydrodynamic focusing and are individually aligned along the central flow axis. Oriented in such a manner, they leave the nozzle with the fluid common having a circular cross section. After leaving the hydrodynamic focusing nozzle, the stream of fluid divides after a short distance into individual droplets containing discrete particles or cells, respectively. Corresponding to the optical information obtained from the cells or particles during the passage through the measuring volume, which lies in the undisturbed region of the stream of fluid, they are deflected into different directions and sorted.

In one variation of this system, the measuring volume does not lie in the region of the upstream cuvette which is free of flow. It is here insignificant whether a further entraining fluid is used to compensate pressure losses. All experimental and commercial cytometric flow sorters involve embodiments in which the entrained stream of carrier fluid has a circular cross section.

However, the optical representation, or image, of the cells or particles disposed in such a stream of fluid is distorted in the plane perpendicular to the direction of flow by the carrier fluid which, because of its circular cross section, acts as a cylindrical lens. This makes planar representation of the center of the fluid column impossible. Moreover, the diffraction and reflection properties of the transition from the optically denser medium of the carrier fluid to the optically less dense entraining medium, which may be air, change the polarization properties of the light passing through these interfaces. With the recent increase of polarization optical examinations involving immunocompetent cells and image analysis in flow, this seems to be of particular significance for the future. An analysis of light scattering in a circular fluid steam is possible only in the direction parallel to the direction of the flow, whereas in a rectangular flow stream the correct imaging properties can be obtained and all solid angles within the forward lobe can be detected without distortion.

SUMMARY OF THE INVENTION

It is an object of the present invention to avoid the above-mentioned drawbacks.

Objects according to the invention are achieved, in apparatus for hydrodynamically focusing particles to permit counting and classification of the particles, which apparatus includes a flow nozzle terminating in a capillary nozzle that forms a thin stream containing the particles and having a circular cross section with the particles oriented along one axis of the thin stream, and a jacket pipe enclosing the capillary nozzle for providing an entraining stream for the thin stream of particles leaving the capillary nozzle, by the provision of a further flow nozzle located downstream of the capillary nozzle and presenting a rectangular exit cross section for receiving the stream leaving the capillary nozzle, and changing its cross section from circular to rectangular such that the stream exists from the further nozzle with a rectangular cross section, means directing a laser beam normally to one flat side of the rectangular cross section at a location downstream of the further nozzle, and a radiation detector disposed for detecting radiation resulting from impingement of laser radiation on particles in the stream of rectangular cross section.

The essential advantages of the invention are that, due to the presence of planar interfaces between media having different indices of refraction, it becomes possible to use axially symmetrical optical systems to produce a high resolution image. Moreover, the fluid column forms its own "windows" which are not subject to any soiling or contamination.

The use of planar fluid/air interfaces makes possible the use of axially symmetrically optical systems having a high aperture number. This is of particular advantage in the examination of extinction, stray light, or light scattering, and fluorescence. The polarization properties of transmitted or emitted light, respectively, are not changed during their passage normal to the planar surfaces. Thus, for the first time it is possible in principle to obtain high resolution images, and possibly even holographic analyses, of the particles disposed in the fluid stream.

BRIEF DESCRIPTION OF THE DRAWING

FIG. 1 is a perspective, pictorial view of a preferred embodiment of apparatus according to the invention.

FIG. 2 is an elevational detail view of a portion of the apparatus of FIG. 1.

DESCRIPTION OF THE PREFERRED EMBODIMENT

In the flow nozzle structure shown in FIG. 1 there is effected, as already disclosed in Offenlegungsschrift No. 2,543,310 and U.S. Pat. No. 4,110,043, a concentric hydrodynamic focusing and individualizing of the cells and particles to form, with the aid of an entraining stream introduced at 11, a thin stream 4 centered on a flow axis 10. The cells are delivered through an inlet 14 and a carrier fluid is introduced through an inlet 15 into a flow nozzle 13 which tapers down to a capillary nozzle 2 having an exit opening 1 of circular cross section. The entraining stream 11 is introduced into the housing 12 outside of the flow nozzle 12 and entrains the thin stream 4 only beginning at the exit opening 1 of the capillary nozzle 2. The dimensions of the various components can be as disclosed in the above-cited prior art.

The entraining fluid 11 enveloping the flow nozzle 2, 13, flows in the same direction along axis 10, entrains the stream 4 formed of the fluid and the cells and transports it on. At the point defined by exit opening 1 in the flow system, the particles or cells, respectively, are individually aligned in a single file stream as required for measurement.

The flow chamber 12 into which the entraining fluid 11 and the central stream 4 now enter, is reduced in size once more downstream of opening 1 to form a nozzle 3 having not a circular but a rectangular cross section. The cross section of nozzle 3 may be square. After a short period of dwell in this nozzle 3 which enforces the formation of a corresponding rectangular fluid stream, the fluid enters, as a rectangular stream 5, into a region defined by a mass of air or other gaseous medium. In the air, for a length of about 15 mm, the fluid stream 5 retains its rectangular, for example, square, shape before it reverts to an approximately round cross section and then breaks up into droplets. Within the region where there exists the approximately square flow cross section, the surface 7 of the fluid faces is of excellent optical quality.

A laser beam 6 passing normally through, for example, face 7, experiences no distortion whatsoever. The forced formation of uniform droplets is possible similarly to that achieved with the conventional cylindrical fluid cross sections. The transmitting or emitting radiation 9 is recorded by a detector 8 and evaluated in a known manner. The radiation system can be constructed and operated in the manner disclosed in the above-cited prior art including backwards fluorescence detection.

The detail view of FIG. 2 shows the exit opening 1 of the capillary nozzle 2 with the particle stream 4 formed by the sample 14 and the diluting, or carrier, solution or buffer 15, respectively, along the axis 10 in housing 12. Concentrically with this axis 10, the further flow nozzle 3 is arranged in the end of housing 12. The inlet opening of nozzle 3 has a circular cross section and is disposed in front of the exit opening 1 to collect the thin stream emerging from nozzle 2 as well as the entraining fluid 11. The circular cross section of the inlet end of this nozzle 3 changes progressively to the rectangular cross section of its outlet portion so that the thin stream 5 exiting therefrom has a correspondingly rectangular cross section. In one exemplary embodiment we have the following dimensions (see FIG. 2): $a=0.2$ mm, $b=0.1$ mm, $c=0.004$ mm, $d=0.5$ mm. The flow rate of stream 5 may be selected between 1.5 m/sec and 12 m/sec. The fluids introduced via inlets 11 and 15 have equal indices of refraction. The numerical aperture typically used presently is n.a.$=0.65$ or higher.

It will be understood that the above description of the present invention is susceptible to various modifications, changes and adaptations, and the same are intended to be comprehended within the meaning and range of equivalents of the appended claims.

What is claimed is:

1. In an apparatus for hydrodynamically focusing particles to permit counting and classification of the particles, which apparatus includes a flow nozzle terminating in a capillary nozzle that forms a thin stream containing the particles and having a circular cross section with the particles oriented along one axis of the thin stream, and a jacket pipe enclosing the capillary nozzle for providing an entraining stream for the thin stream of particles leaving the capillary nozzle, the improvement comprising: a further flow nozzle located downstream of said capillary nozzle and presenting a rectangular cross section for receiving the composite stream composed of the stream leaving said capillary nozzle and said entraining stream, and changing the composite stream cross section from circular to rectangular such that the stream exits from said further nozzle with a rectangular cross section; means directing a laser beam normally to one flat side of the rectangular cross section at a location downstream of said further nozzle; and a radiation detector disposed for detecting radiation resulting from impingement of laser radiation on particles in the stream of rectangular cross section.

2. Apparatus as defined in claim 1 wherein said further flow nozzle is oriented to be coaxial with the flow axis of the thin stream in said capillary nozzle for receiving the thin stream and the entraining stream, and is configured to vary progressively from a circular cross section at its inlet end to said rectangular cross section at its exit end.

3. Apparatus as defined in claim 1 or 2 wherein said further flow nozzle has a square exit cross section.

4. Apparatus as defined in claim 1 or 2 wherein the portion of said further nozzle presenting a rectangular cross section is defined by four walls extending to the outlet end of said further nozzle and delimiting, at the outlet end of said further nozzle, a closed rectangle.

* * * * *